United States Patent
Arakawa et al.

(10) Patent No.: US 10,753,038 B2
(45) Date of Patent: Aug. 25, 2020

(54) OIL SOLUTION FOR CARBON FIBER PRECURSORS AND CARBON FIBER PRECURSOR

(71) Applicant: TAKEMOTO YUSHI KABUSHIKI KAISHA, Gamagori-shi (JP)

(72) Inventors: Yasunobu Arakawa, Gamagori (JP); Hiroki Honda, Gamagori (JP)

(73) Assignee: TAKEMOTO YUSHI KABUSHIKI KAISHA, Gamagori-Shi (JP)

( * ) Notice: Subject to any disclaimer, the term of this patent is extended or adjusted under 35 U.S.C. 154(b) by 0 days.

(21) Appl. No.: 16/317,441

(22) PCT Filed: Jul. 14, 2017

(86) PCT No.: PCT/JP2017/025665
§ 371 (c)(1),
(2) Date: Jan. 11, 2019

(87) PCT Pub. No.: WO2018/100787
PCT Pub. Date: Jun. 7, 2018

(65) Prior Publication Data
US 2019/0234014 A1    Aug. 1, 2019

(30) Foreign Application Priority Data
Dec. 2, 2016 (JP) ................. 2016-234910

(51) Int. Cl.
| | | |
|---|---|---|
| *D06M 15/643* | (2006.01) | |
| *D01F 9/24* | (2006.01) | |
| *D06M 13/473* | (2006.01) | |
| *D06M 15/65* | (2006.01) | |
| *D06M 13/402* | (2006.01) | |
| *C08L 83/06* | (2006.01) | |
| *D06M 13/463* | (2006.01) | |
| *D06M 15/53* | (2006.01) | |
| *D06M 13/17* | (2006.01) | |
| *C07D 233/22* | (2006.01) | |
| *C07F 9/09* | (2006.01) | |
| *C08L 83/08* | (2006.01) | |
| *C08G 77/14* | (2006.01) | |
| *C08G 77/26* | (2006.01) | |
| *C07F 9/11* | (2006.01) | |
| *D06M 13/192* | (2006.01) | |

(52) U.S. Cl.
CPC ......... *D06M 15/6436* (2013.01); *C08L 83/06* (2013.01); *D01F 9/24* (2013.01); *D06M 13/17* (2013.01); *D06M 13/192* (2013.01); *D06M 13/402* (2013.01); *D06M 13/463* (2013.01); *D06M 13/473* (2013.01); *D06M 15/53* (2013.01); *D06M 15/643* (2013.01); *D06M 15/65* (2013.01); *C07D 233/22* (2013.01); *C07F 9/09* (2013.01); *C07F 9/11* (2013.01); *C08G 77/14* (2013.01); *C08G 77/26* (2013.01); *C08L 83/08* (2013.01); *C08L 2201/04* (2013.01)

(58) Field of Classification Search
CPC .. D06M 15/65; D06M 15/6436; D06M 15/53; D06M 13/473; D06M 13/463; D06M 13/192; D06M 13/402; D06M 13/17; D01F 9/24; C08L 2201/04; C08L 83/08; C08L 83/06; C07D 233/22; C07F 9/09; C07F 9/11; C08G 77/14; C08G 77/26
See application file for complete search history.

(56) References Cited

U.S. PATENT DOCUMENTS

| | | | |
|---|---|---|---|
| 4,659,623 | A | 4/1987 | Yoshinari et al. |
| 4,727,177 | A | 2/1988 | Saiki et al. |
| 2012/0021125 | A1 | 1/2012 | Nakayama et al. |

FOREIGN PATENT DOCUMENTS

| | | | | |
|---|---|---|---|---|
| EP | 2735644 | A1 | 5/2014 | |
| JP | 58214581 | A | 12/1983 | |
| JP | 59228069 | A | 12/1984 | |
| JP | 60181368 | A | 9/1985 | |
| JP | 61108767 | A | 5/1986 | |
| JP | 6392781 | A | 4/1988 | |
| JP | 291226 | A | 3/1990 | |
| JP | 491276 | A | 3/1992 | |
| JP | 10102380 | A | 4/1998 | |
| JP | 10298864 | A | 11/1998 | |
| JP | 201024582 | A | 2/2010 | |
| JP | 2010174408 | A | 8/2010 | |
| JP | 2014-105396 | * | 6/2014 | .......... D06M 13/292 |
| JP | 201552176 | A | 3/2015 | |
| JP | 2015221957 | A | 12/2015 | |
| WO | 2016024451 | A1 | 2/2016 | |

OTHER PUBLICATIONS

Search Report for International Patent Application No. PCT/JP2017/025665 dated Aug. 8, 2017.
English Translation of the International Preliminary Report on Patentability dated Jun. 19, 2019 in International Application No. PCT/JP2017/025665 and English Translation of Written Opinion Of The International Searching Authority, issued in International Application No. PCT/JP2017/025665, dated Aug. 8, 2017; 5 pages.
Written Opinion Of The International Searching Authority, issued in International Application No. PCT/JP2017/025665, dated Aug. 8, 2017; 3 pages.

(Continued)

*Primary Examiner* — Amina S Khan
(74) *Attorney, Agent, or Firm* — Cantor Colburn LLP

(57) ABSTRACT

An oil agent for a carbon fiber precursor is provided that contains a base component, a cationic surfactant, and a nonionic surfactant, wherein the cationic surfactant is a specific nitrogen-containing compound.

5 Claims, No Drawings

(56) References Cited

OTHER PUBLICATIONS

Mexican Office Action and English Translation of Mexican Office Action issued in Mexican Patent Application No. MX/a/2019/002016, dated Oct. 17, 2019; 8 pages.

* cited by examiner

OIL SOLUTION FOR CARBON FIBER PRECURSORS AND CARBON FIBER PRECURSOR

TECHNICAL FIELD

The present invention relates to an oil agent for a carbon fiber precursor, and more specifically relates to an oil agent for a carbon fiber precursor in which the oil agent enables imparting excellent antistatic properties and convergence properties to the carbon fiber precursor and enables suppressing the production of rust in a machine for producing a carbon fiber precursor. The present invention also relates to a carbon fiber precursor to which such an oil agent for a carbon fiber precursor adheres.

BACKGROUND ART

An oil agent for a carbon fiber precursor containing an ester compound and a nitrogen-containing surfactant (see, for example, Patent Document 1); an oil agent for a carbon fiber precursor containing a modified silicone, a polybasic acid, and a salt derived therefrom (see, for example, Patent Document 2); an oil agent for a carbon fiber precursor containing a modified silicone and an alkaline compound (see, for example, Patent Document 3); an oil agent for a carbon fiber precursor containing an ester compound and a water-soluble amide compound (see, for example, Patent Document 4); and an oil agent for a carbon fiber precursor containing an amino-modified silicone, a nonionic surfactant, and an antistatic agent (see, for example, Patent Document 5) have been known conventionally. However, problems thereof are that antistatic properties and convergence properties that each of the conventional oil agents for a carbon fiber precursor imparts to a carbon fiber precursor are insufficient, and that a machine for producing a carbon fiber precursor rusts easily.

PRIOR ART DOCUMENTS

Patent Documents

Patent Document 1: Japanese Laid-Open Patent Publication No. 58-214581
Patent Document 2: Japanese Laid-Open Patent Publication No. 10-102380
Patent Document 3: Japanese Laid-Open Patent Publication No. 2-91226
Patent Document 4: Japanese Laid-Open Patent Publication No. 2010-024582
Patent Document 5: Japanese Laid-Open Patent Publication No. 2015-221957

SUMMARY OF THE INVENTION

Problems that are to be Solved by the Invention

A problem to be solved by the present invention is to provide an oil agent for a carbon fiber precursor in which the oil agent enables imparting excellent antistatic properties and convergence properties to the carbon fiber precursor, consequently enables improving process passability of the carbon fiber precursor during production, and suppressing the production of rust in a machine for producing a carbon fiber precursor, and to provide a carbon fiber precursor to which such an oil agent for a carbon fiber precursor adheres.

Means for Solving the Problems

The inventors of the present invention have investigated to solve the above-mentioned problem and consequently found that an oil agent for a carbon fiber precursor containing a base component, a nonionic surfactant, and a specific cationic surfactant is surely suitable.

Specifically, the present invention relates to an oil agent for a carbon fiber precursor containing a base component, a cationic surfactant, and a nonionic surfactant, wherein the cationic surfactant is a compound represented by the following Chemical Formula 1. The present invention also relates to a carbon fiber precursor to which this oil agent for a carbon fiber precursor adheres.

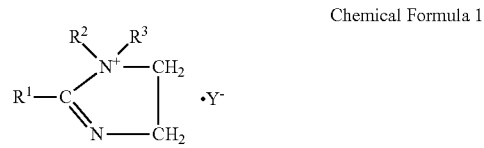

Chemical Formula 1

In Chemical Formula 1,
$R^1$: an aliphatic hydrocarbon group having 6 to 18 carbon atoms,
$R^2$: a hydroxyethyl group, a hydroxypropyl group, or an alkyl group having 1 to 7 carbon atoms,
$R^3$: an alkyl group having 1 to 4 carbon atoms, and
Y: a methylsulfate group, an ethylsulfate group, or an organic group represented by the following Chemical Formula 2.

Chemical Formula 2

In Chemical Formula 2,
$R^4$, $R^5$: an alkyl group having 1 to 4 carbon atoms or a hydrogen atom.

First, the oil agent for a carbon fiber precursor according to the present invention (hereinafter referred to as the oil agent of the present invention) will be described. The oil agent of the present invention contains a base component, a nonionic surfactant, and a specific cationic surfactant.

Although the base component used in the oil agent of the present invention is not particularly limited, at least one selected from an epoxy-modified silicone that is liquid at 25° C., an amino-modified silicone that is liquid at 25° C., and an amide-modified silicone that is liquid at 25° C. is preferable. These sold commercially may be used, and examples of the epoxy-modified silicone that is liquid at 25° C. include the trade name SF-8413 produced by Dow Corning Toray Co., Ltd. (viscosity at 25° C.: 17000 mm$^2$/s, epoxy equivalent: 3800 g/mol), the trade name BY16-876 produced by Dow Corning Toray Co., Ltd. (viscosity at 25° C.: 2400 mm$^2$/s, epoxy equivalent: 2800 g/mol), and the trade name X-22-343 produced by Shin-Etsu Chemical Co., Ltd. (viscosity of 25° C.: 25 mm$^2$/s, epoxy equivalent: 620 g/mol). Examples of the amino-modified silicone that is liquid at 25° C. include the trade name KF-880 produced by Shin-Etsu Chemical Co., Ltd. (viscosity at 25° C.: 650 mm$^2$/s, amino equivalent: 1800 g/mol), the trade name KF-8012 produced by Shin-Etsu Chemical Co., Ltd. (viscosity of 25° C.: 90 mm$^2$/s, amino equivalent: 2200 g/mol), the trade name KF-8008 produced by Shin-Etsu Chemical Co., Ltd. (viscosity of 25° C.: 450 mm$^2$/s, amino equivalent: 5700 g/mol), the trade name KF-8005 produced by Shin-Etsu Chemical Co., Ltd. (viscosity of 25° C.: 1200 mm$^2$/s, amino equivalent: 11000 g/mol), the trade name KF-860 produced by Shin-Etsu Chemical Co., Ltd. (viscosity of 25° C.: 250 mm$^2$/s, amino equivalent: 7600 g/mol), the trade name KF-393 produced by Shin-Etsu Chemical Co., Ltd. (viscosity at 25° C.: 70 mm$^2$/s, amino equivalent: 350 g/mol), the trade name FZ-3505 produced by Dow Corning Toray Co., Ltd. (viscosity at 25° C.: 90 mm$^2$/s, amino equivalent: 4000 g/mol), the trade name BY16-872 produced by Dow Corning Toray Co., Ltd. (viscosity of 25° C.: 20000 mm$^2$/s, amino equivalent: 1800 g/mol), the trade name TSF4702 produced by Momentive Performance Materials Japan LLC (viscosity at 25° C.: 500 mm$^2$/s, amino equivalent: 1600 g/mol), and the trade name TSF4706 produced by Momentive Performance Materials Japan LLC (viscosity 25° C.: 50 mm$^2$/s, amino equivalent: 1600 g/mol). Examples of the amide-modified silicone that is liquid at 25° C. include the trade name KF-3935 produced by Shin-Etsu Chemical Co., Ltd. (viscosity at 25° C.: 25 mm$^2$/s). Especially the amino-modified silicone that is liquid at 25° C. is more preferable. These can be used singly or in combinations of two or more.

The base component that is used in the oil agent of the present invention and is liquid at 25° C. is a substance having a viscosity of 270000 mm$^2$/s or less at 25° C.

The cationic surfactant used in the oil agent of the present invention is a compound represented by the above-mentioned Chemical Formula 1. In Chemical Formula 1, $R^1$ is an aliphatic hydrocarbon group having 6 to 18 carbon atoms, such as a hexyl group, a heptyl group, an octyl group, a decyl group, a decenyl group, an undecyl group, an undecenyl group, a dodecyl group, a dodecenyl group, a tridecyl group, a tridecenyl group, a tetradecyl group, a tetradecenyl group, a pentadecyl group, a pentadecenyl group, a hexadecyl group, a hexadecenyl group, a heptadecyl group, a heptadecenyl group, an octadecyl group, or an octadecenyl group. $R^2$ is a hydroxyethyl group, a hydroxypropyl group, or an alkyl group having 1 to 7 carbon atoms. Specifically, examples of the hydroxyethyl group include 1-hydroxyethyl group and 2-hydroxyethyl group, examples of the hydroxypropyl group include 1-hydroxypropyl group, 2-hydroxypropyl group, and 3-hydroxylpropyl group, and examples of the alkyl group having 1 to 7 carbon atoms include a methyl group, an ethyl group, a propyl group, a butyl group, a pentyl group, a hexyl group, and a heptyl group. $R^3$ is an alkyl group having 1 to 4 carbon atoms, such as a methyl group, an ethyl group, a propyl group, and a butyl group. $Y^-$ is a methylsulfate group, an ethylsulfate group, or an organic group represented by the above-mentioned Chemical Formula 2. In Chemical Formula 2, $R^4$ and $R^5$ are an alkyl group having 1 to 4 carbon atoms, such as a methyl group, an ethyl group, a propyl group, or a butyl group, or a hydrogen atom. Among them, the cationic surfactant is preferably at least one selected from a compound represented by Chemical Formula 1 in which $Y^-$ 1 is a methylsulfate group and a compound represented by Chemical Formula 1 in which $Y^-$ is an ethylsulfate group. These can be used singly or in combinations of two or more.

A method for synthesizing the compound represented by Chemical Formula 2 is not particularly limited, and examples thereof include a method of producing an imidazoline compound by the amidation reaction and cyclodehydration reaction of N-2-hydroxyethylamino ethyl amine with a fatty acid having a predetermined number of carbon atoms and then reacting dimethyl sulfate or diethyl sulfate, which is a quaternizing agent, or an alkyl phosphate with the imidazoline compound.

Although the type of the nonionic surfactant used in the oil agent of the present invention is not particularly limited, examples thereof include compounds obtained by adding ethylene oxide and/or propylene oxide to alcohols or carboxylic acids such as the following (1) to (10): (1) linear alkyl alcohols, such as methanol, ethanol, propanol, butanol, pentanol, hexanol, octanol, nonanol, decanol, undecanol, dodecanol, tridecanol, tetradecanol, pentadecanol, hexadecanol, heptadecanol, octadecanol, nonadecanol, eicosanol, heneicosanol, docosanol, tricosanol, tetracosanol, pentacosanol, hexacosanol, heptacosanol, octacosanol, nonacosanol, and triacontanol; (2) branched alkyl alcohols, such as isopropanol, isobutanol, isohexanol, 2-ethylhexanol, isononanol, isodecanol, isotridecanol, isotetradecanol, isotriacontanol, isohexadecanol, isoheptadecanol, isooctadecanol, isononadecanol, isoeicosanol, isoheneicosanol, isodocosanol, isotricosanol, isotetracosanol, isopentacosanol, isohexacosanol, isoheptacosanol, isooctacosanol, isononacosanol, and isopentadecanol; (3) linear alkenyl alcohols, such as tetradecenol, hexadecenol, heptadecenol, octadecenol, and nonadecenol; (4) branched alkenyl alcohols, such as isohexadecenol and isooctadecenol; (5) cyclic alkyl alcohols, such as cyclopentanol and cyclohexanol; (6) linear alkyl carboxylic acids, such as octanoic acid, nonanoic acid, decanoic acid, undecanoic acid, dodecanoic acid, tridecanoic acid, tetradecanoic acid, pentadecanoic acid, hexadecane acid, heptadecanoic acid, octadecanoic acid, nonadecanoic acid, eicosanoic acid, heneicosanoic acid, and docosanoic acid; (7) branched alkyl carboxylic acids, such as 2-ethylhexanoic acid, isododecanoic acid, isotridecanoic acid, isotetradecanoic acid, isohexadecanoic acid, and isooctadecanoic acid; (8) linear alkenyl carboxylic acids, such as octadecenoic acid, octadecadienoic acid, and octadecatrienoic acid; (9) aromatic alcohols, such as phenol, benzyl alcohol, monostyrenated phenol, distyrenated phenol, and tristyrenated phenol; and (10) aromatic carboxylic acids, such as benzoic acid. Among them, the nonionic surfactant is preferably a compound obtained by addition reaction of ethylene oxide at a ratio of 1 to 50 mol with 1 mol of an organic alcohol having 4 to 40 carbon atoms, which is, for example, a linear alkenyl alcohol, such as butanol, pentanol, hexanol, octanol, nonanol, decanol, undecanol, dodecanol, tridecanol, tetradecanol, pentadecanol, hexadecanol, heptadecanol, octadecanol, nonadecanol, or eicosanol; a branched alkyl alcohol, such as isobutanol, isohexanol, 2-ethyl hexanol, isononanol, isodecanol, isotridecanol, or isotetradecanol; a linear alkenyl alcohol, such as tetradecenol, hexadecenol, heptadecenol, octadecenol, or nonadecenol; or an aromatic alcohol, such as phenol, benzyl alcohol, monostyrenated phenol, distyrenated phenol, or tristyrenated phenol. These nonionic surfactants can be used singly or in combinations of two or more.

Although the ratio of the base component, the cationic surfactant, and the nonionic surfactant is not particularly limited in the oil agent of the present invention, an oil agent is preferable that contains 50 to 95% by mass of the base component, 0.01 to 30% by mass of the cationic surfactant, and 3 to 45% by mass of the nonionic surfactant such that the total content of the base component, the cationic surfactant, and the nonionic surfactant is 100% by mass.

It is preferable that the oil agent of the present invention further contain an organic polybasic acid salt. Examples of the organic polybasic acid salt include butanedioates, alkenyl succinates, 2-hydroxybutanedioates, 2-hydroxypropane-1,2,3-tricarboxylates, pentane-1,5-dicarboxylates, hexanedioates, propanedioates, tartrates, phthalates, cis-butenedioates, trans-butenedioates, trimellitates, and pyromellitates, and among them, an alkali metal salt or amine salt of an organic polybasic acid, such as potassium butanedioate, dipotassium alkenyl succinate, diethanolamine succinate, disodium citrate, or diethanolamine phthalate is preferable.

When the oil agent of the present invention further contains an organic polybasic acid salt, the oil agent preferably contains 50 to 95% by mass of the base component, 0.01 to 30% by mass of the cationic surfactant, 3 to 45% by mass of the nonionic surfactant, and 15% by mass or less of the organic polybasic acid salt such that the total content of the base component, the cationic surfactant, the nonionic surfactant, and the organic polybasic acid salt is 100% by mass.

Next, the carbon fiber precursor according to the present invention (hereinafter referred to as the precursor of the present invention) will be described. The precursor of the present invention is a carbon fiber precursor to which the oil agent of the present invention adheres.

Although the ratio at which the oil agent of the present invention is adhered to a carbon fiber precursor is not particularly limited, the oil agent of the present invention is adhered to a carbon fiber precursor preferably at 0.2 to 1.5% by mass and more preferably at 0.3 to 1.2% by mass. As the method for adhering the oil agent of the present invention, a well-known method can be applied, and examples thereof include immersion oiling method, roller oiling method, and guide oiling method using a metering pump.

Effect of the Invention

According to the present invention, excellent antistatic properties and convergence properties can be imparted to a carbon fiber precursor, process passability of the carbon fiber precursor during production can be consequently improved, and the production of rust in a machine for producing a carbon fiber precursor can be suppressed.

EXAMPLES

Although Examples and the like will be mentioned hereinafter to make the constitution and the effect of the present invention more specific, the present invention is not limited to these Examples. In the following Examples and Comparative Examples, parts means parts by mass and % means % by mass.

Test Section 1 (Provision of Base Components)
The following base components were provided.
A-1: Amino-modified polyorganosiloxane in which the kinematic viscosity at 25° C. is 650 mm$^2$/S, and the amino equivalent is 1800 g/mol (trade name KF-880 produced by Shin-Etsu Chemical Co., Ltd.)
A-2: Amino-modified polyorganosiloxane in which the kinematic viscosity at 25° C. is 90 mm$^2$/S, and the amino equivalent is 2200 g/mol (trade name KF-8012 produced by Shin-Etsu Chemical Co., Ltd.)
A-3: Amino-modified polyorganosiloxane in which the kinematic viscosity at 25° C. is 450 mm$^2$/S, and the amino equivalent is 5700 g/mol (trade name KF-8008 produced by Shin-Etsu Chemical Co., Ltd.)
A-4: Amino-modified polyorganosiloxane in which the kinematic viscosity at 25° C. is 250 mm$^2$/S, and the amino equivalent is 7600 g/mol (trade name KF-860 produced by Shin-Etsu Chemical Co., Ltd.)
A-5: Epoxy-modified polyorganosiloxane in which the kinematic viscosity at 25° C. is 17000 mm$^2$/S and epoxy equivalent: 3800 g/mol (trade name SF-8413 produced by Dow Corning Toray Co., Ltd.)

Test Section 2 (Synthesis of Cationic Surfactants)
Synthesis of B-1
A flask was charged with 282 g (1 mol) of octadecenoic acid and 104 g (1 mol) of N-2-hydroxyethylamino ethylamine. Reaction was performed for 8 hours with the mixture maintained at 180° C. while produced water was distilled off by a nitrogen air flow to obtain 350 g of 1-(2-hydroxyethyl)-2-heptadecenyl-2-imidazoline. Then, 175 g (0.5 mol) of the obtained 1-(2-hydroxyethyl)-2-heptadecenyl 2-imidazoline was warmed to 70 to 90° C. Quaternization reaction was performed by gradually dropping 77 g (0.5 mol) of diethyl sulfate thereinto with stirring at the same temperature. After the dropping, aging was performed for 2 hours at the same temperature to then obtain 252 g of a reaction product. When the obtained reaction product was analyzed, it was 1-(2-hydroxyethyl)-1-ethyl-2-heptadecenyl-2-imidazolinium ethosulfate. This was used as a cationic surfactant B-1.

Synthesis of B-2
A flask was charged with 144 g (1 mol) of octanoic acid and 102 g (1 mol) of N-propylamino ethylamine. Reaction was performed for 8 hours with the mixture maintained at 180° C. while produced water was distilled off by a nitrogen air flow to obtain 210 g of 1-propyl-2-heptyl-2-imidazoline. Then, 105 g (0.5 mol) of the obtained 1-propyl-2-heptyl-2-imidazoline was melted by warming it to 70 to 90° C. Quaternization reaction was then performed by gradually dropping 63 g (0.5 mol) of dimethyl sulfate thereinto with stirring at the same temperature. After the dropping, aging was performed for 2 hours at the same temperature to then obtain 168 g of a reaction product. When the obtained reaction product was analyzed, it was 1-propyl-1-methyl-2-heptyl-2-imidazolinium methosulfate. This was used as a cationic surfactant B-2.

Synthesis of B-3
A flask was charged with 200 g (1 mol) of dodecanoic acid and 118 g (1 mol) of N-3-hydroxypropylamino ethylamine. Reaction was performed for 8 hours with the mixture maintained at 180° C. while produced water was distilled off by a nitrogen air flow to obtain 282 g of 1-(3-hydroxypropyl)-2-undecyl-2-imidazoline. Then, 141 g (0.5 mol) of the obtained 1-(3-hydroxypropyl)-2-undecyl-2-imidazoline was melted by warming it to 70 to 90° C. Quaternization reaction was then performed by gradually dropping 77 g (0.5 mol) of diethyl sulfate thereinto with stirring at the same temperature. After the dropping, aging was performed for 2 hours at the same temperature to then obtain 218 g of a reaction product. When the obtained reaction product was analyzed, it was 1-(3-hydroxypropyl)-1-ethyl 2-undecyl-2-imidazolinium ethosulfate. This was used as a cationic surfactant B-3.

Synthesis of B-4
A flask was charged with 284 g (1 mol) of octadecanoic acid and 104 g (1 mol) of N-2-hydroxyethylamino ethylamine. Reaction was performed for 8 hours with the mixture maintained at 180° C. while produced water was distilled off by a nitrogen air flow to obtain 352 g of 1-(2-hydroxyethyl)-2-heptadecyl-2-imidazoline. Then, 176 g (0.5 mol) of the obtained 1-(2-hydroxyethyl)-2-heptadecyl-2-imidazoline was warmed to 70 to 90° C. Quaternization reaction was performed by gradually dropping 77 g (0.5 mol) of diethyl sulfate thereinto with stirring at the same temperature. After the dropping, aging was performed for 2 hours at the same temperature to then obtain 253 g of a reaction product. When the obtained reaction product was analyzed, it was 1-(2-hydroxyethyl)-1-ethyl-2-heptadecyl-2-imidazolinium ethosulfate. This was used as a cationic surfactant B-4.

Synthesis of B-5

A flask was charged with 200 g (1 mol) of dodecanoic acid and 104 g (1 mol) of N-2-hydroxyethylamino ethylamine. Reaction was performed for 8 hours with the mixture maintained at 180° C. while produced water was distilled off by a nitrogen air flow to obtain 268 g of 1-(2-hydroxyethyl)-undecyl-2-imidazoline. Then, 134 g (0.5 mol) of the obtained 1-(2-hydroxyethyl)-undecyl-2-imidazoline was warmed to 80° C. with stirring in a nitrogen atmosphere. Reaction was performed with the reaction temperature maintained at 80 to 85° C. by dropping 70 g (0.5 mol) of trimethyl phosphate thereinto over 10 minutes. Aging was performed at the same temperature for 3 hours to obtain 204 g of a reaction product. When the obtained reaction product was analyzed, it was a quaternized product of 1-(2-hydroxyethyl)-undecyl-2-imidazoline. This was used as a cationic surfactant B-5.

Synthesis of B-6

A flask was charged with 296 g (1 mol) of nonadecenoic acid and 102 g (1 mol) of N-propylamino ethyl amine. Reaction was performed for 8 hours with the mixture maintained at 180° C. while produced water was distilled off by a nitrogen air flow to obtain 362 g of 1-propyl-2-octadecenyl-2-imidazoline. Then, 181 g (0.5 mol) of the obtained 1-propyl-2-octadecenyl-2-imidazoline was warmed to 80° C. with stirring in a nitrogen atmosphere. Reaction was performed with the reaction temperature maintained at 80 to 85° C. by dropping 91 g (0.5 mol) of triethyl phosphate thereinto over 10 minutes. Aging was performed at the same temperature for 3 hours to obtain 272 g of a reaction product. When the obtained reaction product was analyzed, it was a quaternized product of 1-propyl 2-octadecenyl-2-imidazoline. This was used as a cationic surfactant B-6.

Synthesis of B-7

A flask was charged with 158 g (1 mol) of nonanoic acid and 104 g (1 mol) of N-2-hydroxyethylamino ethylamine. Reaction was performed for 8 hours with the mixture maintained at 180° C. while produced water was distilled off by a nitrogen air flow to obtain 226 g of 1-(2-hydroxyethyl)-octyl-2-imidazoline. Then, 113 g (0.5 mol) of the obtained 1-(2-hydroxyethyl)-octyl-2-imidazoline was warmed to 80° C. with stirring in a nitrogen atmosphere. Reaction was performed with the reaction temperature maintained at 80 to 85° C. by dropping 91 g (0.5 mol) of triethyl phosphate thereinto over 10 minutes. Aging was performed at the same temperature for 3 hours to obtain 204 g of a reaction product. When the obtained reaction product was analyzed, it was a quaternized product of 1-(2-hydroxyethyl)-octyl 2-imidazoline. This was used as a cationic surfactant B-7.

The contents of the cationic surfactants synthesized above were summarized and shown in Table 1.

TABLE 1

| | Chemical Formula 1 | | | | Chemical Formula 2 | |
| --- | --- | --- | --- | --- | --- | --- |
| Type | $R^1$ | $R^2$ | $R^3$ | $Y^-$ | $R^4$ | $R^5$ |
| B-1 | Heptadecenyl group | 2-Hydroxyethyl group | Ethyl group | Ethylsulfate group | — | — |
| B-2 | Heptyl group | Propyl group | Methyl group | Methylsulfate group | — | — |
| B-3 | Undecyl group | 3-Hydroxypropyl group | Ethyl group | Ethylsulfate group | — | — |
| B-4 | Heptadecyl group | 2-Hydroxyethyl group | Ethyl group | Ethylsulfate group | — | — |
| B-5 | Undecyl group | 2-Hydroxyethyl group | Methyl group | Organic group represented by Chemical Formula 2 | Methyl group | Methyl group |
| B-6 | Octadecenyl group | Propyl group | Ethyl group | Organic group represented by Chemical Formula 2 | Ethyl group | Ethyl group |
| B-7 | Octyl group | 2-Hydroxyethyl group | Ethyl group | Organic group represented by Chemical Formula 2 | Ethyl group | Ethyl group |

The following were provided as rB-1 to rB-3.

rB-1: Water-soluble amide compound obtained by cationizing, with diethyl sulfate, an amide compound obtained by reacting diethylene triamine and docosanoic acid rB-2: Dialkylethylmethylammonium ethosulfate (trade name Arquad 2HT-50ES produced by Lion Akzo Co., Ltd.)

rB-3: Dodecyltrimethylammonium chloride (trade name QUARTAMIN 24P produced by Kao Corporation)

Test Section 3 (Synthesis of Nonionic Surfactants)

Synthesis of C-1: An autoclave was charged with 186 g (1.0 mol) of dodecan-1-ol and 1 g of potassium hydroxide, and gas therein was purged with nitrogen gas. The mixture was warmed to 120° C., and 308 g (7 mol) of ethylene oxide was forced thereinto and reacted therewith. After 1-hour aging reaction, the catalyst was removed by adsorbent treatment to obtain a reaction product. When the obtained reaction product was analyzed, it was a compound comprising one dodecan-1-ol group and a total of seven oxyethylene units in one molecule. This was used as a nonionic surfactant C-1.

The following nonionic surfactants were synthesized in the same manner as the nonionic surfactant C-1 or provided.

C-2: Polyoxyethylene (n=5) octyl ether
C-3: Polyoxyethylene (n=40) docosanyl ether
C-4: Polyoxyethylene alkyl ether (trade name SOFTANOL 50 produced by NIPPON SHOKUBAI CO., LTD.)
C-5: Polyoxyethylene (n=40) octadecyl ether
C-6: Polyoxyethylene (n=10) nonylphenyl ether
rC-1: Octadecene β-octadecylthiopropionate
rC-2: Dioctyloctadecene amine oxide
rC-3: Polyethylene glycol (n=8) hexadecanoate
rC-4: Polyoxyethylene (n=30) hydrogenated castor oil ether
rC-5: Triisodecyl trimellitate Test Section 4 (Provision of Organic Polybasic Acid Salts)

The following organic polybasic acid salts were provided.
D-1: Diethanolamine phthalate
D-2: Dipotassium dodecenylsuccinate D-3: Calcium dodecenylsuccinate
rD-1: Potassium octadecanoate
Test Section 5 (Provision of Other Compounds)
The following other compounds were provided.
rX-1: Ammonium acetate
rX-2: Ammonium hydroxide salt
Test Section 6 (Preparation of Oil Agents for Carbon Fiber Precursor)

Example 1

First, 140 g of the base component A-1, 30 g of the cationic surfactant B-1, 20 g of the nonionic surfactant C-1, and 10 g of the organic polybasic acid salt D-1, which were synthesized or provided in Test Sections 1 to 5 were added in a beaker and well mixed. An aqueous 50% liquid of the oil agent of Example 1 was prepared by adding ion-exchanged water to the mixture gradually with stirring continuously such that the solid content concentration was 50%.

Example 2

Similarly to Example 1, 110 g of the base component A-2, 20 g of the cationic surfactant B-2, 50 g of the nonionic surfactant C-2, and 20 g of the organic polybasic acid salt D-2 were added in a beaker and well mixed, and an aqueous 50% liquid of the oil agent of Example 2 was prepared by adding ion-exchanged water to the mixture gradually with stirring continuously such that the solid content concentration was 50%.

Example 3

Similarly to Example 1, 170 g of the base component A-3, 8 g of the cationic surfactant B-2, 20 g of the nonionic surfactant C-3, and 2 g of the organic polybasic acid salt D-1 were added in a beaker and well mixed, and an aqueous 50% liquid of the oil agent of Example 3 was prepared by adding ion-exchanged water to the mixture gradually with stirring continuously such that the solid content concentration was 50%.

Example 4

Similarly to Example 1, 190 g of the base component A-4, 6 g of the cationic surfactant B-3, 6 g of the nonionic surfactant C-4, and 1 g of the organic polybasic acid salt D-2 were added in a beaker and well mixed, and an aqueous 50% liquid of the oil agent of Example 4 was prepared by adding ion-exchanged water to the mixture gradually with stirring continuously such that the solid content concentration was 50%.

Example 5

Similarly to Example 1, 120 g of the base component A-2, 14 g of the cationic surfactant B-4, 60 g of the nonionic surfactant C-5, and 6 g of the organic polybasic acid salt D-2 were added in a beaker and well mixed, and an aqueous 50% liquid of the oil agent of Example 5 was prepared by adding ion-exchanged water to the mixture gradually with stirring continuously such that the solid content concentration was 50%.

Example 6

Similarly to Example 1, 150 g of the base component A-1, 40 g of the cationic surfactant B-3, 26 g of the nonionic surfactant C-6, and 4 g of the organic polybasic acid salt D-2 were added in a beaker and well mixed, and an aqueous 50% liquid of the oil agent of Example 6 was prepared by adding ion-exchanged water to the mixture gradually with stirring continuously such that the solid content concentration was 50%.

Example 7

Similarly to Example 1, 160 g of the base component A-3, 20 g of the cationic surfactant B-1, 10 g of the nonionic surfactant C-4, and 10 g of the organic polybasic acid salt D-2 were added in a beaker and well mixed, and an aqueous 50% liquid of the oil agent of Example 7 was prepared by adding ion-exchanged water to the mixture gradually with stirring continuously such that the solid content concentration was 50%.

Example 8

Similarly to Example 1, 60 g of the base component A-3, 10 g of the cationic surfactant B-2, 120 g of the nonionic surfactant C-3, and 10 g of the organic polybasic acid salt D-3 were added in a beaker and well mixed, and an aqueous 50% liquid of the oil agent of Example 8 was prepared by adding ion-exchanged water to the mixture gradually with stirring continuously such that the solid content concentration was 50%.

Example 9

Similarly to Example 1, 50 g of the base component A-1, 40 g of the cationic surfactant B-1, 90 g of the nonionic surfactant C-2, and 20 g of the organic polybasic acid salt D-3 were added in a beaker and well mixed, and an aqueous 50% liquid of the oil agent of Example 9 was prepared by adding ion-exchanged water to the mixture gradually with stirring continuously such that the solid content concentration was 50%.

Example 10

Similarly to Example 1, 176 g of the base component A-2, 8 g of the cationic surfactant B-3, 6 g of the nonionic surfactant C-1, and 10 g of the C-4 were added in a beaker and well mixed, and an aqueous 50% liquid of the oil agent of Example 10 was prepared by adding ion-exchanged water to the mixture gradually with stirring continuously such that the solid content concentration was 50%.

Example 11

Similarly to Example 1, 130 g of the base component A-2, 20 g of the cationic surfactant B-2, and 50 g of the nonionic surfactant C-3 were added in a beaker and well mixed, and an aqueous 50% liquid of the oil agent of Example 11 was prepared by adding ion-exchanged water to the mixture gradually with stirring continuously such that the solid content concentration was 50%.

Example 12

Similarly to Example 1, 40 g of the base component A-1, 20 g of the cationic surfactant B-4, and 140 g of the nonionic surfactant C-5 were added in a beaker and well mixed, and an aqueous 50% liquid of the oil agent of Example 12 was prepared by adding ion-exchanged water to the mixture gradually with stirring continuously such that the solid content concentration was 50%.

Example 13

Similarly to Example 1, 104 g of the base component A-5, 16 g of the cationic surfactant B-5, and 80 g of the nonionic surfactant C-2 were added in a beaker and well mixed, and an aqueous 50% liquid of the oil agent of Example 13 was prepared by adding ion-exchanged water to the mixture gradually with stirring continuously such that the solid content concentration was 50%.

Example 14

Similarly to Example 1, 170 g of the base component A-5, 4 g of the cationic surfactant B-6, and 26 g of the nonionic surfactant C-3 were added in a beaker and well mixed, and an aqueous 50% liquid of the oil agent of Example 14 was prepared by adding ion-exchanged water to the mixture gradually with stirring continuously such that the solid content concentration was 50%.

Example 15

Similarly to Example 1, 130 g of the base component A-5, 10 g of the cationic surfactant B-7, and 60 g of the nonionic surfactant C-2 were added in a beaker and well mixed, and an aqueous 50% liquid of the oil agent of Example 15 was prepared by adding ion-exchanged water to the mixture gradually with stirring continuously such that the solid content concentration was 50%.

Comparative Example 1

Similarly to Example 1, 176 g of the base component A-1 and 24 g of the nonionic surfactant C-4 were added in a beaker and well mixed, and an aqueous 50% liquid of the oil agent of Comparative Example 1 was prepared by adding ion-exchanged water to the mixture gradually with stirring continuously such that the solid content concentration was 50%.

Comparative Example 2

Similarly to Example 1, 30 g of the nonionic surfactant C-6, 120 g of the rC-1, 20 g of the rC-2, 20 g of the rC-3, and 10 g of the rC-4 were added in a beaker and well mixed, and an aqueous 50% liquid of the oil agent of Comparative Example 2 was prepared by adding ion-exchanged water to the mixture gradually with stirring continuously such that the solid content concentration was 50%.

Comparative Example 3

Similarly to Example 1, 120 g of the base component A-2, 46 g of the A-5, 30 g of the nonionic surfactant C-4, and 4 g of the rX-1 were added in a beaker and well mixed, and an aqueous 50% liquid of the oil agent of Comparative Example 3 was prepared by adding ion-exchanged water to the mixture gradually with stirring continuously such that the solid content concentration was 50%.

Comparative Example 4

Similarly to Example 1, 199.4 g of the base component A-2 and 0.6 g of the rX-2 were added in a beaker and well mixed, and an aqueous 50% liquid of the oil agent of Comparative Example 4 was prepared by adding ion-exchanged water to the mixture gradually with stirring continuously such that the solid content concentration was 50%.

Comparative Example 5

Similarly to Example 1, 160 g of the nonionic surfactant C-1 and 40 g of the organic polybasic acid salt D-1 were added in a beaker and well mixed, and an aqueous 50% liquid of the oil agent of Comparative Example 5 was prepared by adding ion-exchanged water to the mixture gradually with stirring continuously such that the solid content concentration was 50%.

Comparative Example 6

Similarly to Example 1, 30 g of the cationic surfactant rB-1, 80 g of the nonionic surfactant C-1, and 90 g of the rC-5 were added in a beaker and well mixed, and an aqueous 50% liquid of the oil agent of Comparative Example 6 was prepared by adding ion-exchanged water to the mixture gradually with stirring continuously such that the solid content concentration was 50%.

Comparative Example 7

Similarly to Example 1, 140 g of the base component A-2, 40 g of the nonionic surfactant C-4, and 20 g of the organic polybasic acid salt rD-1 were added in a beaker and well mixed, and an aqueous 50% liquid of the oil agent of Comparative Example 7 was prepared by adding ion-exchanged water to the mixture gradually with stirring continuously such that the solid content concentration was 50%.

Comparative Example 8

Similarly to Example 1, 172 g of the base component A-4, 4 g of the cationic surfactant rB-2, and 24 g of the nonionic surfactant C-1 were added in a beaker and well mixed, and an aqueous 50% liquid of the oil agent of Comparative Example 8 was prepared by adding ion-exchanged water to the mixture gradually with stirring continuously such that the solid content concentration was 50%.

Comparative Example 9

Similarly to Example 1, 172 g of the base component A-4, 4 g of the cationic surfactant rB-3 and 24 g of the nonionic surfactant C-1 were added in a beaker and well mixed, and an aqueous 50% liquid of the oil agent of Comparative Example 9 was prepared by adding ion-exchanged water to the mixture gradually with stirring continuously such that the solid content concentration was 50%.

The contents of the oil agents for a carbon fiber precursor of the examples prepared above were summarized and shown in Table 2.

TABLE 2

| Section | | Base component Type | Ratio (%) | Cationic surfactant Type | Ratio (%) | Nonionic surfactant Type | Ratio (%) | Polybasic acid salt Type | Ratio (%) | Other Type | Ratio (%) |
|---|---|---|---|---|---|---|---|---|---|---|---|
| Ex. | 1 | A-1 | 70 | B-1 | 15 | C-1 | 10 | D-1 | 5 | — | — |
| | 2 | A-2 | 55 | B-2 | 10 | C-2 | 25 | D-2 | 10 | — | — |
| | 3 | A-3 | 85 | B-2 | 4 | C-3 | 10 | D-1 | 1 | — | — |
| | 4 | A-4 | 95 | B-3 | 1.5 | C-4 | 3 | D-2 | 0.5 | — | — |
| | 5 | A-2 | 60 | B-4 | 7 | C-5 | 30 | D-2 | 3 | — | — |
| | 6 | A-1 | 75 | B-3 | 20 | C-6 | 13 | D-2 | 2 | — | — |
| | 7 | A-3 | 80 | B-1 | 10 | C-4 | 5 | D-2 | 5 | — | — |
| | 8 | A-3 | 30 | B-2 | 5 | C-3 | 60 | D-3 | 5 | — | — |
| | 9 | A-1 | 25 | B-1 | 20 | C-2 | 45 | D-3 | 10 | — | — |
| | 10 | A-2 | 88 | B-3 | 4 | C-1 | 3 | — | — | — | — |
| | | | | | | C-4 | 5 | | | | |
| | 11 | A-2 | 65 | B-2 | 10 | C-3 | 25 | — | — | — | — |
| | 12 | A-1 | 20 | B-4 | 10 | C-5 | 70 | — | — | — | — |
| | 13 | A-5 | 52 | B-5 | 8 | C-2 | 40 | — | — | — | — |
| | 14 | A-5 | 85 | B-6 | 2 | C-3 | 13 | — | — | — | — |
| | 15 | A-5 | 65 | B-7 | 5 | C-2 | 30 | — | — | — | — |
| Com. Ex. | 1 | A-1 | 88 | — | — | C-4 | 12 | — | — | — | — |
| | 2 | — | — | — | — | C-6 | 15 | — | — | — | — |
| | | | | | | rC-1 | 60 | | | | |
| | | | | | | rC-2 | 10 | | | | |
| | | | | | | rC-3 | 10 | | | | |
| | | | | | | rC-4 | 5 | | | | |
| | 3 | A-5 | 23 | — | — | C-4 | 15 | — | — | rX-1 | 2 |
| | | A-2 | 60 | | | | | | | | |
| | 4 | A-2 | 99.7 | — | — | — | — | — | — | rX-2 | 0.3 |
| | 5 | — | — | — | — | C-1 | 80 | D-1 | 20 | — | — |
| | 6 | — | — | rB-1 | 15 | C-1 | 40 | — | — | — | — |
| | | | | | | rC-5 | 45 | | | | |
| | 7 | A-2 | 70 | — | — | C-4 | 20 | rD-1 | 10 | — | — |
| | 8 | A-4 | 86 | rB-2 | 2 | C-1 | 12 | — | — | — | — |
| | 9 | A-4 | 86 | rB-3 | 2 | C-1 | 12 | — | — | — | — |

Test Section 7

Adhesion of Oil Agent for a Carbon Fiber Precursor

An aqueous 50% liquid of the oil agent of each example prepared in Test Section 6 was adhered to acrylic filament yarn (75 denier/40 filament) by roller oiling method such that the oil agent for a carbon fiber precursor was 0.5±0.1%, and the yarn was then dried at 115° C. for 4 seconds using a drying roller to obtain sample yarn A. This sample yarn A was used for the evaluation of electric resistance value and generated electricity mentioned below. An aqueous 50% liquid of the oil agent of each example prepared in Test Section 6 was adhered to acrylic filament yarn (16000 denier/12000 filament) by immersion such that the oil agent for a carbon fiber precursor was 0.5±0.1%, and the yarn was then dried at 115° C. for 4 seconds using a drying roller to obtain sample yarn B. This sample yarn B was used for the evaluation of convergence properties mentioned below.

Test Section 8 (evaluation)

Evaluation of Electric Resistance Value

The sample yarn A was left to stand in an atmosphere of 20×65% RH for 24 hours, and a box for measuring electric resistance (40-ml capacity) was charged with 10 g of evaluation sample under the same conditions. The electric resistance (log $\Omega$) was measured using the trade name Insulation Meter SM-5E manufactured by TOA Electronics Ltd., and the electric resistance value was evaluated according to the following criteria.

Evaluation criteria of electric resistance value (log $\Omega$):
∘∘: less than 9
∘: 9 to less than 10
x: 10 to less than 11
xx: 11 or more Evaluation of Generated Electricity The sample yarn A was left to stand in an atmosphere of 20×65% RH for 24 hours and made to travel in contact with a chrome-plated pin subjected to satin finish under the same conditions at an initial tension of 20 g and a yarn speed of 100 m/minute, and the generated electricity after the contact was measured with a current-collecting potential meter (manufactured by KASUGA DENKI, INC.) and evaluated according to the following criteria.

Evaluation Criteria of Generated Electricity
5: Less than 50 volts
4: 50 volts or more to less than 100 volts
3: 100 volts or more to less than 300 volts
2: 300 volts or more to less than 500 volts
1: 500 volts or more Evaluation of Convergence Properties When 50 kg of the sample yarn B was manufactured, the convergence condition of the carbon fiber precursor fiber at the time of passing in each process and being wound was visually observed. The same test was performed 5 times, and the convergence properties were evaluated according to the following criteria.

Evaluation Criteria of Convergence Properties

∘∘: The convergence properties are very good, and there is no problem with process passability at all.

∘: The convergence properties are good, and there is no problem with process passability.

x: The convergence properties are short, and there is a slight problem with process passability.

xx: The convergence properties are inferior, and there is a great problem with process passability.

Evaluation of Rust

Ion-exchanged water was further added to an aqueous 50% liquid of the oil agent for a carbon fiber precursor of each example prepared in Test Section 6 such that the solid content concentration was 2%. A washed metal guide roller was immersed in this aqueous solution, and it was then left to stand at 20° C.×100% RH for 24 hours. The rusting condition of each metal guide roller was visually observed, and the rust was evaluated according to the following criteria.

Evaluation Criteria of Rust

∘: The rusting is not observed.

x: The rusting is observed.

The results of the oil agents for a carbon fiber precursor of the examples evaluated above were summarized and shown in Table 3.

TABLE 3

| | | Evaluation results | | | |
|---|---|---|---|---|---|
| Section | | Electric resistance value | Generated electricity | Convergence properties | Rust |
| Ex. | 1 | ∘∘ | 5 | ∘∘ | ∘ |
| | 2 | ∘∘ | 5 | ∘∘ | ∘ |
| | 3 | ∘∘ | 5 | ∘∘ | ∘ |
| | 4 | ∘∘ | 5 | ∘∘ | ∘ |
| | 5 | ∘∘ | 5 | ∘∘ | ∘ |
| | 6 | ∘∘ | 5 | ∘∘ | ∘ |
| | 7 | ∘∘ | 5 | ∘∘ | ∘ |
| | 8 | ∘∘ | 4 | ∘ | ∘ |
| | 9 | ∘∘ | 4 | ∘ | ∘ |
| | 10 | ∘ | 4 | ∘∘ | ∘ |
| | 11 | ∘ | 4 | ∘∘ | ∘ |
| | 12 | ∘ | 4 | ∘ | ∘ |
| | 13 | ∘ | 3 | ∘ | ∘ |
| | 14 | ∘ | 3 | ∘ | ∘ |
| | 15 | ∘ | 3 | ∘ | ∘ |
| Com. Ex. | 1 | xx | 1 | ∘ | ∘ |
| | 2 | xx | 1 | xx | ∘ |
| | 3 | x | 1 | ∘ | ∘ |
| | 4 | xx | 1 | ∘ | ∘ |
| | 5 | ∘ | 2 | xx | ∘ |
| | 6 | x | 1 | xx | ∘ |
| | 7 | xx | 1 | ∘ | ∘ |
| | 8 | x | 2 | ∘ | ∘ |
| | 9 | ∘ | 3 | ∘ | x |

As is clear from the results of Table 3 corresponding to Table 2, according to the present invention, excellent antistatic properties and convergence properties can be imparted to a carbon fiber precursor, process passability of the carbon fiber precursor during production can be consequently improved, and the production of rust in a machine for producing a carbon fiber precursor can be suppressed.

The invention claimed is:

1. An oil agent for a carbon fiber precursor, comprising a base component,
a cationic surfactant,
a nonionic surfactant, and
an optional organic polybasic acid salt,
wherein the cationic surfactant is a compound represented by Chemical Formula 1:

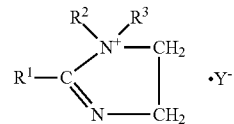

in Chemical Formula 1,
wherein $R^1$ is selected from the group consisting of an alkyl and an alkenyl group having 7 to 18 carbon atoms,
wherein $R^2$ is selected from the group consisting of a hydroxyethyl group, a hydroxypropyl group, and a propyl group,
wherein $R^3$ is selected from the group consisting of a methyl and an ethyl group, and
wherein $Y^-$ is selected from the group consisting of a methylsulfate group, an ethylsulfate group, and an organic group represented by Chemical Formula 2:

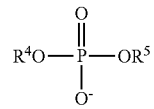

in Chemical Formula 2,
wherein $R^4$, $R^5$ is selected from the group consisting of a methyl and an ethyl group, wherein the base component is an amino-modified silicone that is liquid at 25° C. and the oil agent comprises 50 to 95% by mass of the base component, 0.01 to 30% by mass of the cationic surfactant, 3 to 45% by mass of the nonionic surfactant and 15% by mass or less of the optional organic polybasic acid salt such that the total content of the base component, the cationic surfactant, the nonionic surfactant, and the optional polybasic acid salt is 100% by mass, and wherein the nonionic surfactant is a compound obtained by addition reaction of ethylene oxide and/or propylene oxide to an organic alcohol at a ratio of 1 to 50 mol ethylene oxide and/or propylene oxide with 1 mol of an organic alcohol having 4 to 40 carbon atoms.

2. The oil agent for a carbon fiber precursor according to claim 1, wherein the cationic surfactant is at least one selected from a compound represented by Chemical Formula 1 in which $Y^-$ is a methylsulfate group and a compound represented by Chemical Formula 1 in which $Y^-$ is an ethylsulfate group.

3. The oil agent for a carbon fiber precursor according to claim 1, wherein the organic polybasic acid salt is present.

4. The oil agent for a carbon fiber precursor according to claim 3, wherein the organic polybasic acid salt is an alkali metal salt or amine salt of an organic polybasic acid.

5. A carbon fiber precursor comprising the oil agent of claim 1.

* * * * *